United States Patent
Tashiro et al.

(10) Patent No.: US 11,036,376 B2
(45) Date of Patent: Jun. 15, 2021

(54) ULTRASOUND DIAGNOSIS APPARATUS AND METHOD OF CONTROLLING ULTRASOUND DIAGNOSIS APPARATUS

(71) Applicant: FUJIFILM Corporation, Tokyo (JP)

(72) Inventors: Rika Tashiro, Ashigarakami-gun (JP); Tomoki Inoue, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/804,204

(22) Filed: Feb. 28, 2020

(65) Prior Publication Data
US 2020/0201523 A1 Jun. 25, 2020

Related U.S. Application Data

(63) Continuation of application No. PCT/JP2018/021166, filed on Jun. 1, 2018.

(30) Foreign Application Priority Data

Sep. 14, 2017 (JP) .............................. JP2017-176977

(51) Int. Cl.
*G06F 3/0484* (2013.01)
*A61B 8/00* (2006.01)

(52) U.S. Cl.
CPC .......... *G06F 3/04845* (2013.01); *A61B 8/465* (2013.01)

(58) Field of Classification Search
CPC ............. A61B 8/46–469; G06F 3/0488; G06F 3/04845; G06F 3/04812
See application file for complete search history.

(56) References Cited

U.S. PATENT DOCUMENTS

2006/0132460 A1   6/2006   Kolmykov-Zotov et al.
2013/0324850 A1   12/2013  Petruzzelli et al.
(Continued)

FOREIGN PATENT DOCUMENTS

EP   3028638 A1       6/2016
JP   2006-179006 A    7/2006
(Continued)

OTHER PUBLICATIONS

International Preliminary Report on Patentability and Written Opinion of the International Searching Authority with an English translation (forms PCT/IB373, PCT/ISA/237 and PCT/IB/326), dated Mar. 26, 2020, for corresponding International Application No. PCT/JP2018/021166.
(Continued)

*Primary Examiner* — Michael Pervan
(74) *Attorney, Agent, or Firm* — Birch, Stewart, Kolasch & Birch, LLP

(57) ABSTRACT

An ultrasound diagnosis apparatus including: a touch panel that has a display screen displaying an acquired ultrasound image and allows an input operation of a user; and a processor configured to: generate a caliper and display the caliper on the display screen in such a manner as to be superimposed on the ultrasound image; display, on the display screen, a caliper operation effective region surrounding the caliper, stop displaying the caliper operation effective region in a case where the user touches the caliper operation effective region displayed on the display screen of the touch panel; move the caliper following a movement operation by the user while in touch with the touch panel; and resume the display of the moved caliper operation effective region that surrounds the moved caliper upon a release of the touch by the user.

20 Claims, 7 Drawing Sheets

(56) References Cited

U.S. PATENT DOCUMENTS

| | | | |
|---|---|---|---|
| 2014/0059486 A1* | 2/2014 | Sasaki | G06F 3/0488 |
| | | | 715/810 |
| 2014/0276057 A1 | 9/2014 | Lee et al. | |
| 2016/0120508 A1 | 5/2016 | Kim et al. | |
| 2016/0157825 A1* | 6/2016 | Lee | A61B 8/5223 |
| | | | 600/437 |
| 2017/0090571 A1* | 3/2017 | Bjaerum | A61B 8/4254 |
| 2017/0209125 A1* | 7/2017 | Rai | G06F 3/0488 |
| 2018/0203581 A1 | 7/2018 | Takeda | |
| 2018/0289360 A1* | 10/2018 | Funakubo | G06F 3/0488 |
| 2018/0348983 A1* | 12/2018 | Tanabe | A61B 8/467 |

FOREIGN PATENT DOCUMENTS

| | | |
|---|---|---|
| JP | 2018-110751 A | 7/2006 |
| JP | 2010-142563 A | 7/2010 |
| JP | 2012-19824 A | 2/2012 |
| JP | 2016-516465 A | 6/2016 |

OTHER PUBLICATIONS

International Search Report (form PCT/ISA/210), dated Aug. 7, 2018, for corresponding International Application No. PCT/JP2018/021166, with an English translation.
Extended European Search Report, dated Oct. 2, 2020, for European Application No. 18856481.9.

* cited by examiner

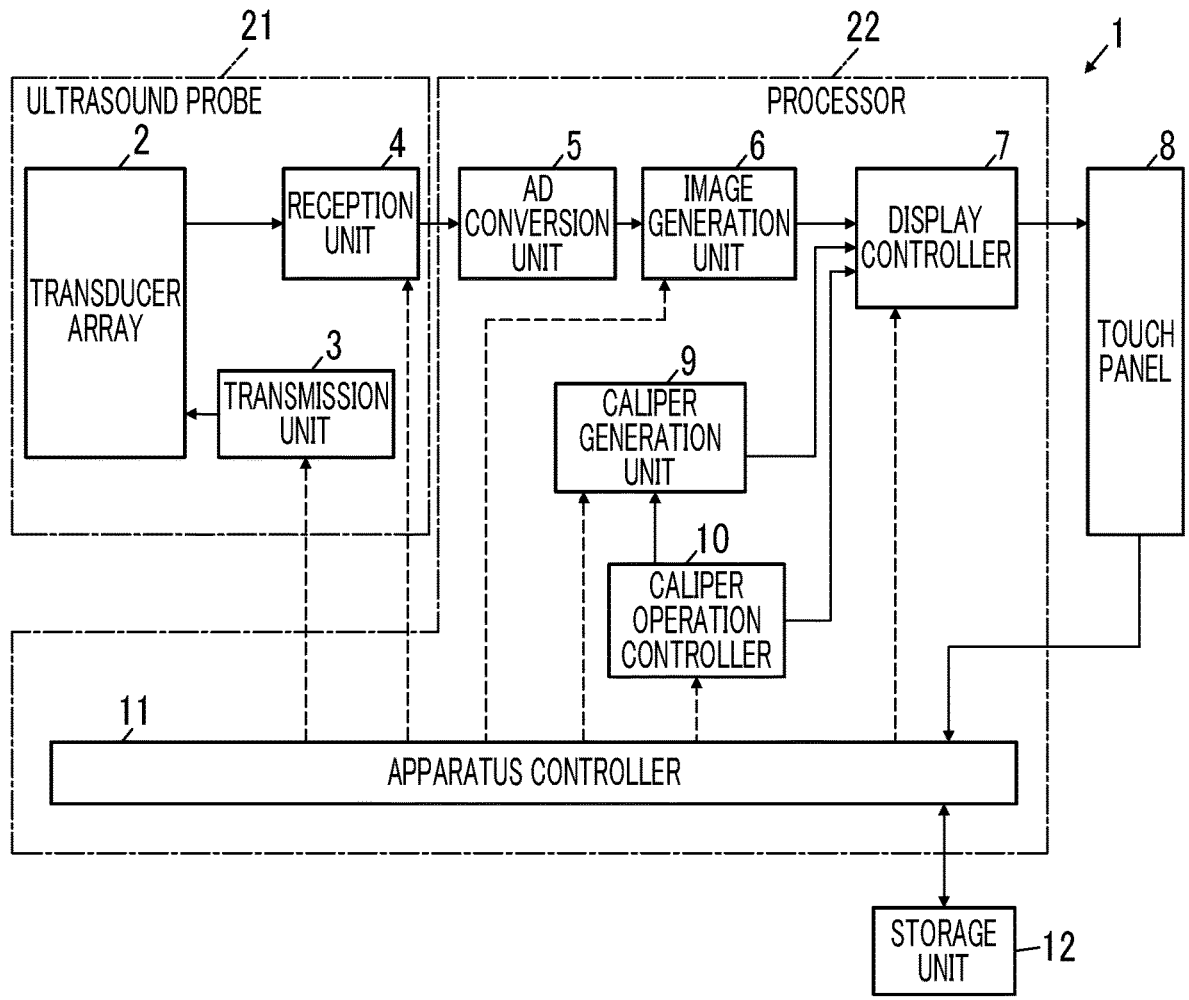
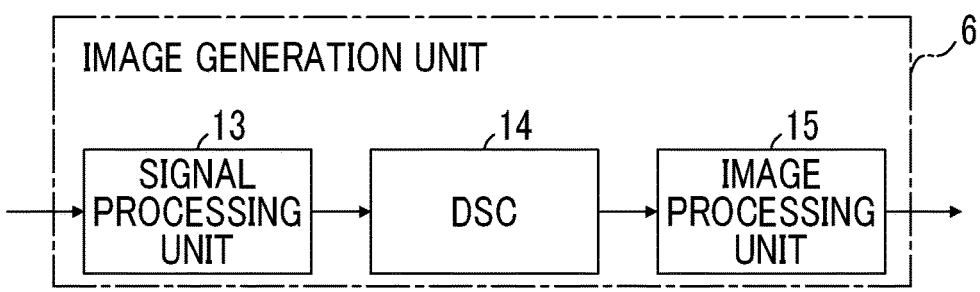

ULTRASOUND DIAGNOSIS APPARATUS AND METHOD OF CONTROLLING ULTRASOUND DIAGNOSIS APPARATUS

CROSS-REFERENCE TO RELATED APPLICATIONS

This application is a Continuation of PCT International Application No. PCT/JP2018/021166 filed on Jun. 1, 2018, which claims priority under 35 U.S.C. § 119(a) to Japanese Patent Application No. 2017-176977 filed on Sep. 14, 2017. Each of the above applications is hereby expressly incorporated by reference, in its entirety, into the present application.

BACKGROUND OF THE INVENTION

1. Field of the Invention

The present invention relates to an ultrasound diagnosis apparatus and a method of controlling an ultrasound diagnosis apparatus, and in particular, to an ultrasound diagnosis apparatus comprising a touch panel and a method of controlling an ultrasound diagnosis apparatus.

2. Description of the Related Art

In recent years, an ultrasound diagnosis apparatus comprising a touch panel has become widespread. In general, the touch panel has a display screen, and receives an input operation with a so-called touch operation to bring a finger of a user, a stylus pen, or the like into contact with or close to the display screen. For this reason, with the ultrasound diagnosis apparatus comprising the touch panel, the user can designate a position on the display screen through a touch operation on the display screen without using an input device, such as a touch pad, a trackball, or a mouse. In such an ultrasound diagnosis apparatus, since the ultrasound diagnosis apparatus can be used more efficiently as the operability of the touch operation is higher, various trials of improving the operability of the touch operation have been conducted.

For example, JP2012-019824A discloses an ultrasound diagnosis apparatus that displays an operation button associated with a caliper at a position a given distance from the caliper displayed on an ultrasound image. In a case where the user moves the displayed operation button while touching the operation button, the caliper is also moved following the movement of the operation button. For this reason, the caliper is prevented from being hidden behind the finger of the user, or the like.

SUMMARY OF THE INVENTION

However, in the ultrasound diagnosis apparatus disclosed in JP2012-019824A, since the operation button is disposed only at a position a given distance from the corresponding caliper in a given direction, in a case where the user touches the operation button, a portion to be viewed by the user in the ultrasound image may be hidden behind the finger of the user, or the like, and as a result, there is a problem in that operability is degraded.

The invention has been accomplished in order to solve the problem in the related art, and an object of the invention is to provide an ultrasound diagnosis apparatus and a method of controlling an ultrasound diagnosis apparatus capable of improving the operability of a touch operation.

In order to achieve the above-described object, the invention provides an ultrasound diagnosis apparatus comprising a touch panel that has a display screen displaying an acquired ultrasound image and allows an input operation of a user, a caliper generation unit that generates a caliper and displays the caliper on the display screen in such a manner as to be superimposed on the ultrasound image, a caliper operation controller that displays, on the display screen, a caliper operation effective region, which surrounds the caliper corresponding to the caliper displayed on the display screen and in which the caliper is moved and operated within the display screen, and an apparatus controller that, in a case where the user touches the caliper operation effective region displayed on the display screen on the touch panel, performs control such that the caliper operation controller stops the display of the caliper operation effective region, in a case where the user moves a touch position on the touch panel while touching the caliper operation effective region, performs control such that the caliper generation unit moves a position of the caliper displayed on the display screen following the movement of the touch position, and in a case where the user releases a touch operation on the touch panel, performs control such that the caliper operation controller resumes the display of the caliper operation effective region, which surrounds the caliper corresponding to the moved position of the caliper.

It is preferable that the caliper operation effective region is a region formed in a circle that is centered on the caliper and has a prescribed radius. The caliper operation controller may display the caliper operation effective region of a set size on the display screen.

The apparatus controller may perform control such that, in a case where the user touches the caliper operation effective region, the caliper operation controller displays, on the display screen, a touch confirmation display region, which is centered on the touch position and is smaller than the caliper operation effective region, instead of the caliper operation effective region. The caliper operation controller may display the touch confirmation display region of a set size on the display screen.

The apparatus controller may perform control such that, in a case where the user touches the caliper operation effective region, the caliper operation controller gradually reduces the caliper operation effective region displayed on the display screen to perform switching to the display of the touch confirmation display region. The apparatus controller may perform control such that, in a case where the user releases a touch operation on the touch panel, the caliper operation controller gradually magnifies the touch confirmation display region displayed on the display screen to perform switching to the display of the caliper operation effective region.

The apparatus controller may perform control such that, in a case where the user touches the caliper operation effective region, the caliper generation unit changes a display color of the caliper displayed on the display screen or makes the caliper blink. The caliper operation controller may display a recommended point representing a recommended candidate of the touch position within the caliper operation effective region on the display screen in such a manner as to be superimposed on the caliper operation effective region.

The invention also provides a method of controlling an ultrasound diagnosis apparatus comprising a touch panel that has a display screen and allows an input operation of a user. The method comprises displaying an acquired ultrasound image, generating a caliper and displaying the caliper on the display screen in such a manner as to be superimposed on the ultrasound image, displaying, on the display screen, a caliper operation effective region, which surrounds the caliper corresponding to the caliper displayed on the display screen and in which the caliper is moved and operated within the display screen, in a case where the user touches the caliper operation effective region displayed on the display screen on the touch panel, stopping the display of the caliper operation effective region, in a case where the user moves a touch position on the touch panel while touching the caliper operation effective region, moving a position of the caliper displayed on the display screen following the movement of the touch position, and in a case where the user releases a touch operation on the touch panel, resuming the display of the caliper operation effective region, which surrounds the caliper corresponding to the moved position of the caliper.

According to the invention, since the ultrasound diagnosis apparatus comprises the apparatus controller that, in a case where the user touches the caliper operation effective region displayed on the display screen on the touch panel, performs control such that the caliper operation controller stops the display of the caliper operation effective region, in a case where the user moves the touch position on the touch panel while touching the caliper operation effective region, performs control such that the caliper generation unit moves the position of the caliper displayed on the display screen following the movement of the touch position, and in a case where the user releases the touch operation on the touch panel, the caliper operation controller resumes the display of the caliper operation effective region, which surrounds the caliper corresponding to the moved position of the caliper, it is possible to improve the operability of the touch operation.

BRIEF DESCRIPTION OF THE DRAWINGS

FIG. 1 is a block diagram showing the configuration of an ultrasound diagnosis apparatus according to Embodiment 1 of the invention.

FIG. 2 is a block diagram showing the internal configuration of an image generation unit in Embodiment 1 of the invention.

DESCRIPTION OF THE PREFERRED EMBODIMENTS

Figure 3:
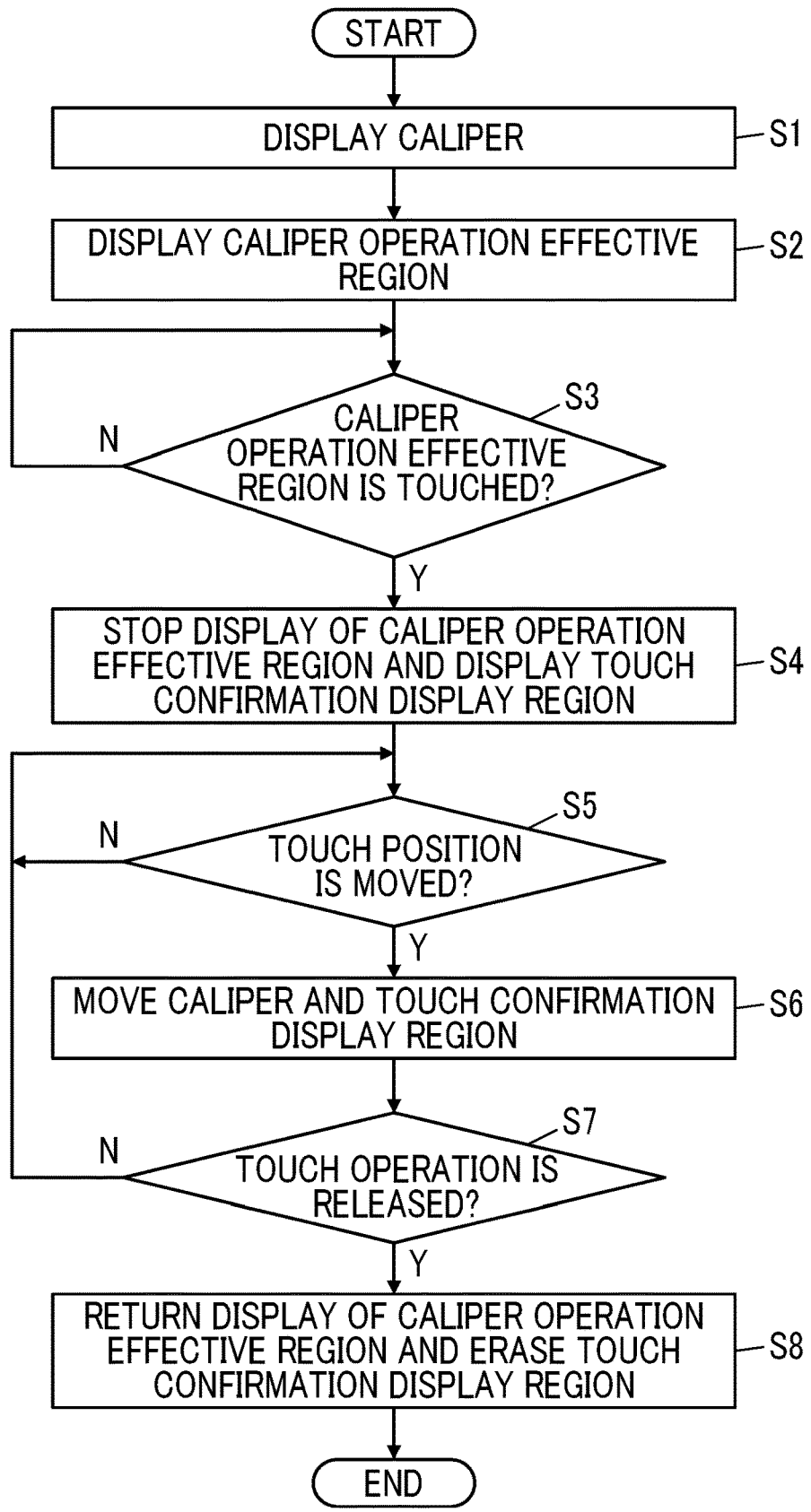
FIG. 3 is a flowchart showing an operation in a case where an operation of a caliper is performed in the ultrasound diagnosis apparatus according to Embodiment 1 of the invention.

Hereinafter, an embodiment of the invention will be described referring to the accompanying drawings.

Embodiment 1

FIG. 1 shows the configuration of an ultrasound diagnosis apparatus 1 according to Embodiment 1 of the invention. As shown in FIG. 1, the ultrasound diagnosis apparatus 1 comprises a transducer array 2, and a transmission unit 3 and a reception unit 4 are connected to the transducer array 2. An analog-to-digital (AD) conversion unit 5, an image generation unit 6, a display controller 7, and a touch panel 8 are sequentially connected to the reception unit 4. A caliper generation unit 9 and a caliper operation controller 10 are connected to the display controller 7, and the caliper generation unit 9 is connected to the caliper operation controller 10. In addition, an apparatus controller 11 is connected to the transmission unit 3, the reception unit 4, the image generation unit 6, the display controller 7, the touch panel 8, the caliper generation unit 9, and the caliper operation controller 10, and a storage unit 12 is connected to the apparatus controller 11. The apparatus controller 11 and the storage unit 12 are connected to each other to deliver information in both directions.

The transducer array 2, the transmission unit 3, and the reception unit 4 constitute an ultrasound probe 21, and the AD conversion unit 5, the image generation unit 6, the display controller 7, the caliper generation unit 9, the caliper operation controller 10, and the apparatus controller 11 constitute a processor 22.

The transducer array 2 of the ultrasound probe 21 shown in FIG. 1 has a plurality of elements (ultrasound transducers) arranged in an one-dimensional or two-dimensional manner. Each element transmits an ultrasonic wave in response to an actuation signal supplied from the transmission unit 3, receives a reflected wave from a subject, and outputs a reception signal. Each element is constituted of a transducer in which electrodes are formed at both ends of a piezoelectric body made of, for example, piezoelectric ceramic represented by lead zirconate titanate (PZT), a polymer piezoelectric element represented by poly vinylidene di fluoride (PVDF), piezoelectric single crystal represented by a lead magnesium niobate-lead titanate (PMN-PT), or the like.

The transmission unit 3 of the ultrasound probe 21 includes, for example, a plurality of pulse generators, and adjusts an delay amount of each actuation signal based on a transmission delay pattern selected in response to a control signal from the apparatus controller 11 such that ultrasonic waves transmitted from a plurality of elements of the transducer array 2 form an ultrasonic beam and supplies the actuation signals to a plurality of elements. In this way, in a case where a pulsed or continuous-wave voltage is applied to the electrodes of each of the elements of the transducer array 2, the piezoelectric body expands and contracts to generate pulsed or continuous-wave ultrasonic waves from the respective transducers. An ultrasonic beam is formed from a combined wave of the ultrasonic waves.

The transmitted ultrasonic beam is reflected by, for example, a target, such as a part of the subject, and propagates toward the transducer array 2 of the ultrasound probe 21. The ultrasonic waves propagating toward the transducer array 2 in this way are received by the respective elements constituting the transducer array 2. In this case, the respective transducers constituting the transducer array 2 expand and contract with reception of the propagating ultrasonic waves to generate electrical signals. The electrical signals are output from the respective elements to the reception unit 4 as reception signals of the ultrasonic waves. Though not shown, the reception unit 4 has an amplification unit that amplifies the reception signals of the ultrasonic waves input from the respective transducers, and in a case where the signals amplified in the amplification unit are converted to digitized element data in the AD conversion unit 5 of the processor 22, the element data is output to the image generation unit 6.

As shown in FIG. 2, the image generation unit 6 of the processor 22 has a configuration in which a signal processing unit 13, a digital scan converter (DSC) 14, and an image processing unit 15 are connected in series. The signal processing unit 13 executes reception focus processing in which a delay is given to each piece of element data according to a set sound speed and addition (phasing addition) is performed based on a reception delay pattern selected in response to a control signal from the apparatus controller 11. Through the reception focus processing, a sound ray signal with narrowed focus of the ultrasonic echo is generated. The signal processing unit 13 performs correction of attenuation due to a propagation distance on the generated sound ray signal according to a depth of a reflection position of the ultrasonic wave, and then, executes envelope detection processing, thereby generating a B mode image signal that is tomographic image information relating to a tissue inside the subject. The B mode image signal generated in this way is output to the DSC 14.

The DSC 14 raster-converts the B mode image signal to an image signal according to a normal television signal scanning system. The image processing unit 15 executes various kinds of needed image processing, such as brightness correction, gradation correction, sharpness correction, and color correction, on image data obtained in the DSC 14 and outputs the B mode image signal to the display controller 7. In the following description, the B mode image signal is referred to as an ultrasound image.

Figure 4:
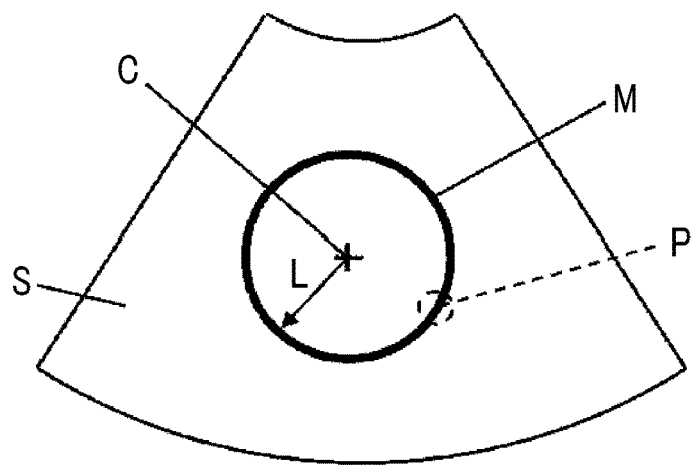
FIG. 4 is a display example of a caliper operation effective region in Embodiment 1 of the invention.

The caliper generation unit 9 of the processor 22 generates a caliper and displays the generated caliper on a display screen of the touch panel 8 described below through the display controller 7 so as to be superimposed on the ultrasound image. Here, the caliper is a cursor that is used to designate a position on the display screen of the touch panel 8. A shape of the caliper is not particularly limited and may be a cross shape or a circular shape as long as the position on the display screen of the touch panel 8 can be designated. FIG. 4 shows a cross-shaped caliper C as an example.

Figure 5:
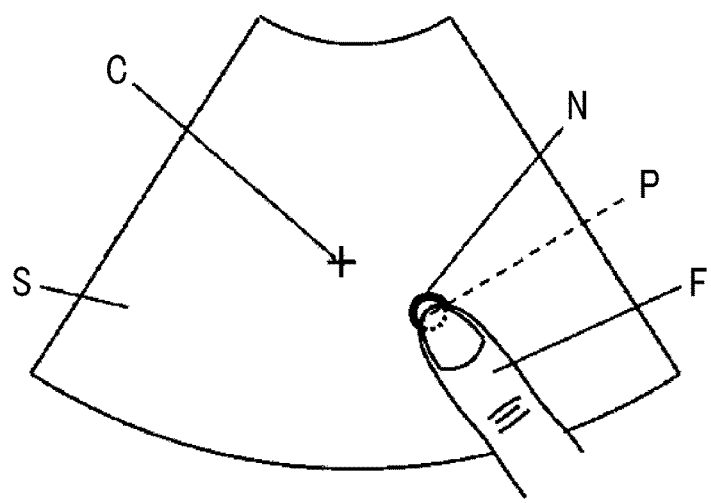
FIG. 5 is a display example of a touch confirmation display region in Embodiment 1 of the invention.

As shown in FIG. 1, the caliper operation controller 10 of the processor 22 displays a caliper operation effective region, which surrounds the caliper corresponding to the caliper displayed on the display screen of the touch panel 8 described below and in which the caliper is moved and operated within the display screen, on the display screen of the touch panel 8 through the display controller 7. The caliper operation effective region is disposed at a given distance from the caliper. For example, FIG. 4 shows a circular caliper operation effective region M that surrounds the caliper C therearound and has a distance from the caliper, that is, a radius L. The caliper operation controller 10 displays a touch confirmation display region, which centers around a touch position of a user on the caliper operation effective region and is smaller than the caliper operation effective region, on the display screen of the touch panel 8. For example, FIG. 5 shows a circular touch confirmation display region N disposed at a touch position with a finger F of the user.

The apparatus controller 11 of the processor 22 performs control of the respective units of the ultrasound diagnosis apparatus 1 based on a touch operation of the user through the touch panel 8. In particular, the apparatus controller 11 performs control according to the touch operation of the user through the touch panel 8 such that the caliper operation controller 10 displays the caliper operation effective region and the touch confirmation display region on the display screen of the touch panel 8. The display control of the caliper operation effective region and the touch confirmation display region of the apparatus controller 11 will be described below in detail.

The display controller 7 of the processor 22 generates a composite image, in which the ultrasound image generated by the image generation unit 6, the caliper generated by the caliper generation unit 9, and the caliper operation effective region and the touch confirmation display region are composed, and makes the generated composite image be displayed on the display screen of the touch panel 8.

The touch panel 8 of the ultrasound diagnosis apparatus 1 has the display screen and displays the composite image, and the user performs the touch operation. The display screen is constituted of, for example, a display device, such as a liquid crystal display (LCD).

The storage unit 12 of the ultrasound diagnosis apparatus 1 stores an operation program and the like of the ultrasound diagnosis apparatus 1, and a recording medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

The AD conversion unit 5, the image generation unit 6, the display controller 7, the caliper generation unit 9, the caliper operation controller 10, and the apparatus controller 11 are constituted of a central processing unit (CPU) and a control program causing the CPU to execute various kinds of processing; however, the units may be constituted using digital circuits. The AD conversion unit 5, the image generation unit 6, the display controller 7, the caliper generation unit 9, the caliper operation controller 10, and the apparatus controller 11 may be incorporated partially or entirely in one CPU. As the CPU executes the control program, the CPU functions as the image generation unit 6, the display controller 7, the caliper generation unit 9, the caliper operation controller 10, and the apparatus controller 11.

Next, an operation of the ultrasound diagnosis apparatus 1 of Embodiment 1 of the invention in operating the caliper will be described in detail referring to a flowchart shown in FIG. 3 and FIGS. 4 to 7. First, in Step S1, as shown in FIG. 4, the caliper generation unit 9 displays the caliper C in such a manner as to be superimposed on an ultrasound image S displayed on the display screen of the touch panel 8. Subsequently, in Step S2, the apparatus controller 11 performs control such that the caliper operation controller 10 displays the circular caliper operation effective region M, which surrounds the caliper C displayed in Step S1 and has a radius L, on the display screen of the touch panel 8.

In Step S3, the apparatus controller 11 determines whether or not the user touches the displayed caliper operation effective region M, that is, the circumference of the circle having the radius L. The apparatus controller 11 is on standby until the user touches the caliper operation effective region M, and in a case where the apparatus controller 11 determines the user touches the caliper operation effective region M, the apparatus controller 11 progresses to Step S4. In the following description, although it is assumed that the user touches the touch position P shown in FIG. 4 for description, the user may touch any spot on the caliper operation effective region M as the touch position P.

In Step S4, the apparatus controller 11 performs control such that, as shown in FIG. 5, the caliper operation controller 10 stops the display of the caliper operation effective region M and displays the touch confirmation display region N smaller than the caliper operation effective region M at the touch position P, instead of the caliper operation effective region M. In FIG. 5, the touch confirmation display region N is displayed so as to be partially hidden behind the finger F of the user and slightly exposed from the tip of the finger F. Subsequently, in Step S5, the apparatus controller 11 determines whether or not the position of the finger F of the user, that is, the touch position P is being moved. The apparatus controller 11 is on standby until the touch position P is moved, and in a case where determination is made that the touch position P is being moved, progresses to Step S6.

Figure 6:
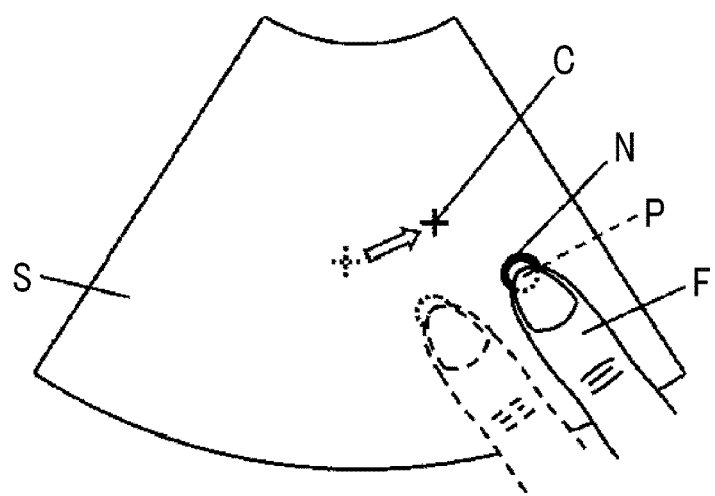
FIG. 6 is an example showing movement of the caliper in Embodiment 1 of the invention.

In Step S6, as shown in FIG. 6, the apparatus controller 11 performs control such that the caliper generation unit 9 moves the caliper C following the movement of the touch position P, and performs control such that the caliper operation controller 10 moves the touch confirmation display region N following the movement of the touch position P. In this case, the caliper C is moved in the same direction and at the same distance as a movement direction and a movement distance of the touch position P and the touch confirmation display region N while maintaining a given distance L to the touch position P and the touch confirmation display region N.

Subsequently, in Step S7, the apparatus controller 11 determines whether or not the touch operation of the user is released, that is, the finger F of the user is detached from the touch position P. The apparatus controller 11 returns to Step S5 in a case where determination is made that the touch operation of the user is not released, determines whether or not the touch position P is being moved, and in a case where the touch position P is being moved, moves the caliper C and the touch confirmation display region N following the touch position P. In this way, while the finger F of the user is touching the touch position P, the touch confirmation display region N is continuously displayed at the touch position P. In Step S7, in a case where the apparatus controller 11 determines that the touch operation of the user is released, the apparatus controller progresses to Step S8.

Figure 7:
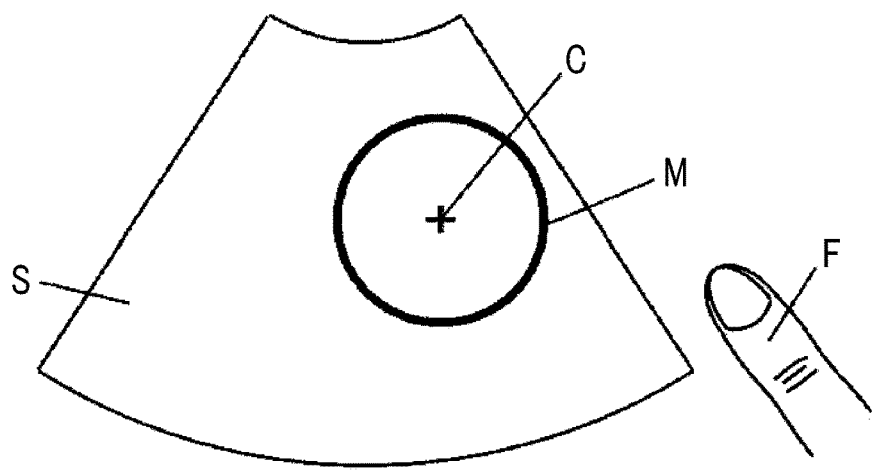
FIG. 7 is an example showing an operation release state of the caliper in Embodiment 1 of the invention.

In Step S8, the apparatus controller 11 performs control such that, as shown in FIG. 7, the caliper operation controller 10 s the display of the caliper operation effective region M corresponding to the moved position of the caliper C and erases the display of the touch confirmation display region N. As a result, only the caliper C and the caliper operation effective region M are displayed in such a manner as to be superimposed on the ultrasound image S.

As described above, with the ultrasound diagnosis apparatus 1 according to the embodiment of the invention, in a case where the user touches the caliper operation effective region M displayed on the display screen of the touch panel 8, the display of the caliper operation effective region M is stopped, and in a case where the user moves the touch position P while touching the caliper operation effective region M, the position of the caliper C is moved following the movement of the touch position P. For this reason, it is possible to allow the user to operate the caliper C while restraining a portion to be viewed by the user in the ultrasound image S from being hidden behind the finger of the user, or the like, and to improve the operability of the touch operation. Furthermore, while the user is touching the caliper operation effective region M, the touch confirmation display region N smaller than the caliper operation effective region M is displayed at the touch position P. For this reason, it is possible to allow the user to visually confirm that the user is operating the caliper C.

Although a circular region is exemplified as the caliper operation effective region M, the shape of the caliper operation effective region M is not particularly limited as long as the caliper operation effective region M is disposed so as to surround the caliper. For example, as the caliper operation effective region M, a polygonal region, such as a triangle or a quadrangle, a region consisting of any closed curve, and a region consisting of a set of a plurality of points arranged on a closed curve can be set. In particular, in a case where the caliper operation effective region M consists of a set of a plurality of points, for example, eight points arranged on a closed curve surrounding the caliper C, only the respective points can be set as the caliper operation effective region M or a non-displayed closed curve, such as a circle, passing through the respective points can also be set as an actual caliper operation effective region M.

The size of the caliper operation effective region M can be set in advance by the user. In this way, as the user can set the size of the caliper operation effective region M, the user can perform an operation of the caliper C conforming to the preference of the user and the ultrasound image S. Thus, it is possible to improve the operability of the touch operation.

The size of the caliper operation effective region M can be changed according to the depth in capturing the ultrasound image S. In general, as the depth in capturing the ultrasound image S is deeper, the size of a tissue in the ultrasound image S is reflected smaller than the size of the entire ultrasound image S. For this reason, in a case where the size of the caliper operation effective region M is changed according to the depth of the ultrasound image S, it is preferable that the caliper operation effective region M is displayed smaller as the depth is deeper, and is displayed greater as the depth is shallower. In general, the depth in capturing the ultrasound image S may be different depending on the kind of the ultrasound probe. For example, a linear ultrasound probe has the depth in capturing the ultrasound image S shallower than in a convex ultrasound probe and a radial ultrasound probe. For this reason, the size of the caliper operation effective region M may be changed depending on the kind of the ultrasound probe that captures the ultrasound image S.

The size of the touch confirmation display region N can be set in advance by the user. For example, in performing the touch operation, there are a case where the finger of the user is used and a case where a stylus pen is used. In general, since the tip of the stylus pen is often finer than the tip of the finger, in a case where the use of one of the finger of the user and the stylus pen in the touch operation is decided, the touch confirmation display region N can be set to have such a size so as to be partially hidden behind the tip of the finger of the user or the stylus pen and slightly exposed from the tip of the finger of the user or the stylus pen. With this, it is possible to allow the user to easily visually recognize that the user is operating the caliper C by moving the touch position P.

Even though the user uses either of the finger of the user or the stylus pen in touching the touch position P on the caliper operation effective region M, the size of the touch confirmation display region N may be set to a given size in advance. The size of the touch confirmation display region N may be set to be smaller than an area of a portion where the tip of the finger of the user or the stylus pen to be used comes into contact with the touch panel 8. In this case, although the touch confirmation display region N is hidden behind the finger of the user or the stylus pen to be used and is not viewed by the user, it is possible to substantially restrain the ultrasound image S from being hidden.

In Embodiment 1, in a case where the user releases the touch operation on the caliper operation effective region M, the display of the touch confirmation display region N is erased, and the display of the caliper operation effective region M is resumed; however, in a case where a given time has elapsed after the touch operation of the user is released, the display of the touch confirmation display region N may be erased, and the display of the caliper operation effective region M may be resumed. In particular, in a case where the size of the touch confirmation display region N is set to be smaller than the thickness of the finger of the user, the stylus pen, or the like, as the user releases the touch operation, it is possible to allow the user to view the positional relationship between the touch confirmation display region N and the caliper operation effective region M hidden behind the finger, the stylus pen, or the like.

While the caliper operation effective region M is being touched by the user, the caliper C can be highlighted. As a method of highlighting the caliper C, for example, changing the color of the caliper C, making the caliper C blink, or the like can be employed. With this, it is possible to allow the user to view that the caliper C is in an operation state.

Though not shown, in a case where the ultrasound image S, on which the caliper C is disposed, is stored in an external memory or the like, it is preferable that only the caliper C or coordinate information of the caliper C is stored in association with the ultrasound image S, and the caliper operation effective region M is not stored. Here, for example, as an operation to store the ultrasound image S, the ultrasound image S and a storage button (not shown) can be displayed on the display screen of the touch panel 8, and as the user touches the storage button, the ultrasound image S can be stored in the external memory (not shown) or the like. In this case, in a case where the caliper C and the caliper operation effective region M are displayed in such a manner as to be superimposed on the ultrasound image S, for example, as the user touches the storage button, the caliper operation effective region M can be erased, and only the ultrasound image S and the caliper C being displayed can be stored. In this case, for example, it is possible to resume the display of the caliper operation effective region M with the completion of the storage of the ultrasound image S and the caliper C as a trigger.

For example, in a case where a predetermined operation is performed, such as the user touching the touch position P on the caliper operation effective region M or the caliper operation effective region M twice for a prescribed period, as the storage button is touched by the user in a state in which the display of the caliper operation effective region M is erased and the caliper operation effective region M is not displayed, only the ultrasound image S and the caliper C being displayed can be stored in the external memory (not shown) or the like. In this case, for example, it is possible to resume the display of the caliper operation effective region M with the touch of the user to the caliper C as a trigger. In this way, in a case where the ultrasound image S, on which the caliper C is disposed, is stored in the external memory or the like, as the caliper operation effective region M is not stored, the caliper operation effective region M can be displayed on the display screen of the touch panel 8 only for the ultrasound image S where an operation of the caliper C is needed.

Embodiment 2

Figure 8:
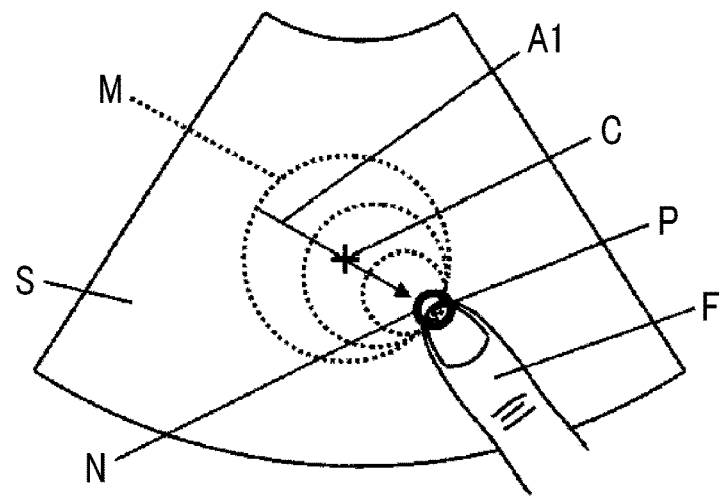
FIG. 8 is a diagram showing a manner in which the caliper operation effective region is gradually reduced to be switched to the display of the touch confirmation display region in Embodiment 2 of the invention.

In Embodiment 1, in a case where the user touches the caliper operation effective region Mc the display of the caliper operation effective region M is stopped, and the touch confirmation display region N is displayed; however, in this case, the display of the caliper operation effective region M may be set to be gradually switched to the display of the touch confirmation display region N, instead of being erased instantly. For example, as shown in FIG. 8, in a case where the user touches the caliper operation effective region M, the caliper operation effective region M is gradually reduced along a direction A1 toward the touch position P and is switched to the display of the touch confirmation display region N. Here, though not shown, an ultrasound diagnosis apparatus of Embodiment 2 has the same configuration as the ultrasound diagnosis apparatus 1 of Embodiment 1 shown in FIG. 1, and the display operations of the caliper operation effective region M and the touch confirmation display region N are made by the apparatus controller 11 shown in FIG. 1 controlling the caliper operation controller 10.

Figure 9:
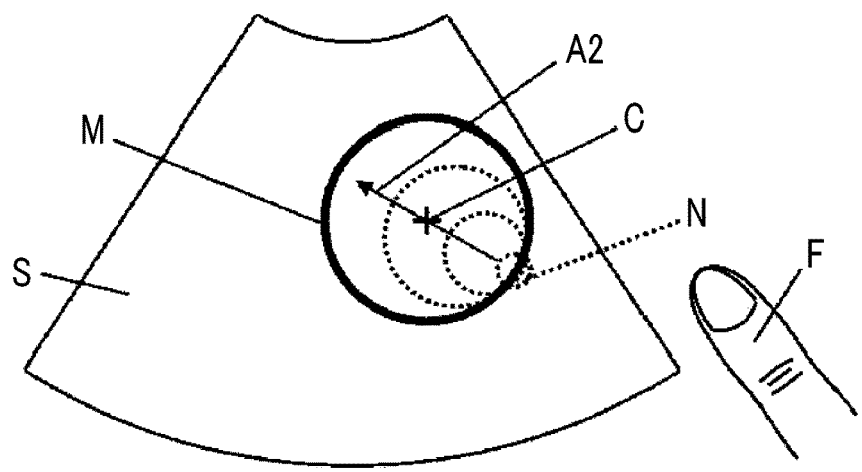
FIG. 9 is a diagram showing a manner in which the touch confirmation display region is gradually magnified to be switched to the display of the caliper operation effective region in Embodiment 2 of the invention.

Similarly, in a case where the user releases the touch operation on the touch panel 8, the display of the touch confirmation display region N can be set to be gradually switched to the display of the caliper operation effective region M, instead of being erased instantly. For example, as shown in FIG. 9, in a case where the user releases the touch operation of the caliper operation effective region M, touch confirmation display region N is gradually magnified along a direction A2 toward the caliper C and is switched to the display of the caliper operation effective region M. Such a display operation is made by the apparatus controller 11 controlling the caliper operation controller 10.

As described above, as the display of the caliper operation effective region M and the display of the touch confirmation display region N are displayed to be gradually switched, it is possible to allow the user to easily view that the corresponding caliper is changed to the operation state and the corresponding caliper is released from the operation state, and to improve the operability of the touch operation.

Embodiment 3

In Embodiment 1, although the embodiment in which the touch confirmation display region N is displayed to be partially hidden behind the finger F of the user and slightly exposed from the tip of the finger F is exemplified, the touch confirmation display region N is not limited thereto.

Figure 10:
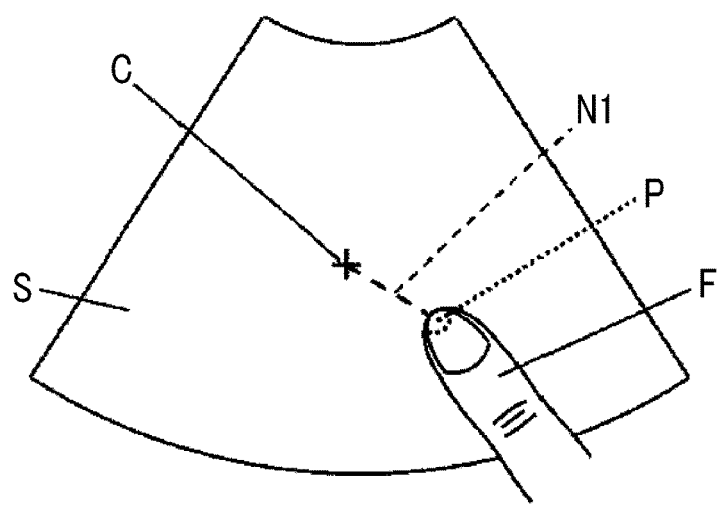
FIG. 10 is a display example of a touch confirmation display region in Embodiment 3 of the invention.
Figure 11:
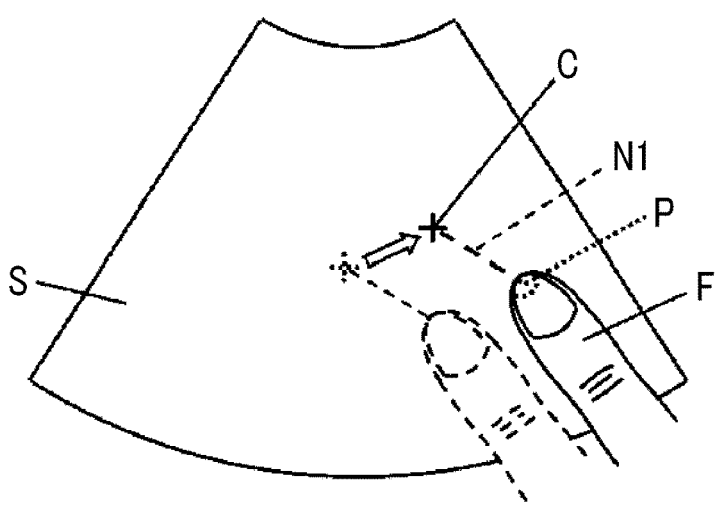
FIG. 11 is an example showing movement of the caliper in Embodiment 3 of the invention.

As shown in FIG. 10, a touch confirmation display region N1 in Embodiment 3 is a line segment connecting the center of the caliper C and the touch position P, and is displayed on the display screen of the touch panel 8 as the user touches the touch position P on the caliper operation effective region M. Similarly to the touch confirmation display region N in Embodiment 1, as shown in FIG. 11, as the user moves the finger F to move the touch position P, the touch confirmation display region N1 is moved following the touch position P. Here, though not shown, an ultrasound diagnosis apparatus of Embodiment 3 has the same structure as the ultrasound diagnosis apparatus 1 of Embodiment 1 shown in FIG. 1, the display operations of the caliper operation effective region M and the touch confirmation display region N1 are made by the apparatus controller 11 shown in FIG. 1 controlling the caliper operation controller 10.

In this way, as the touch confirmation display region N1 is displayed as the line segment connecting the center of the caliper C and the touch position P, it is possible to allow the user to easily visually confirm that the user is operating the caliper C, and to improve the operability of the touch operation.

Figure 12:
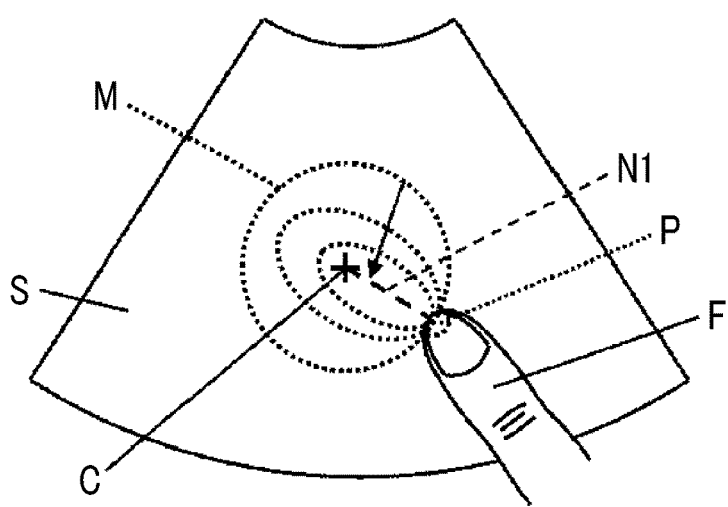
FIG. 12 is a diagram showing a manner in which the caliper operation effective region is gradually reduced to be switched to the display of the touch confirmation display region in Embodiment 3 of the invention.
Figure 13:
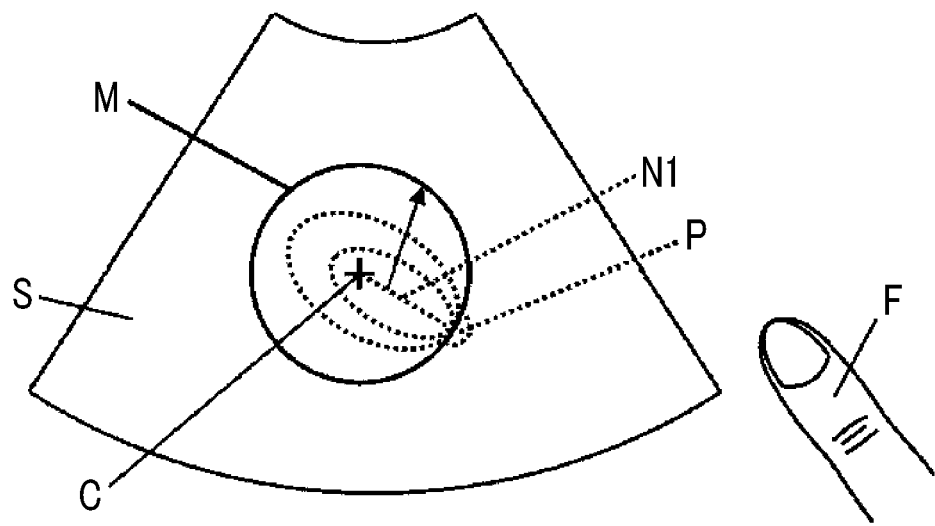
FIG. 13 is a diagram showing a manner in which the display of the touch confirmation display region is gradually switched to the display of the caliper operation effective region in Embodiment 3 of the invention.

In a case where the user touches the caliper operation effective region M, as in Embodiment 1, the display of the caliper operation effective region M can be stopped instantly, and the touch confirmation display region N1 can be displayed instantly; however, as in Embodiment 2, the display of the caliper operation effective region M may be set to be gradually switched to the display of the touch confirmation display region N1. In this case, for example, as shown in FIG. 12, in a case where the user touches the touch position P on the caliper operation effective region M, the display of the caliper operation effective region M is gradually reduced and is switched to the display of the line segment-shaped touch confirmation display region N1. In a case where the user detaches the finger F to release the touch operation, for example, as shown in FIG. 13, the display of the touch confirmation display region N1 is changed to a closed curve shape, such as an ellipse, and is gradually magnified in outline, and is switched to the display of the caliper operation effective region M.

It is preferable that the line segment-shaped touch confirmation display region N1 in Embodiment 3 is a solid line displayed to be transparent or a dotted line, a broken line, or the like in order to restrain the ultrasound image S from being hardly viewed by the user.

Embodiment 4

Figure 14:
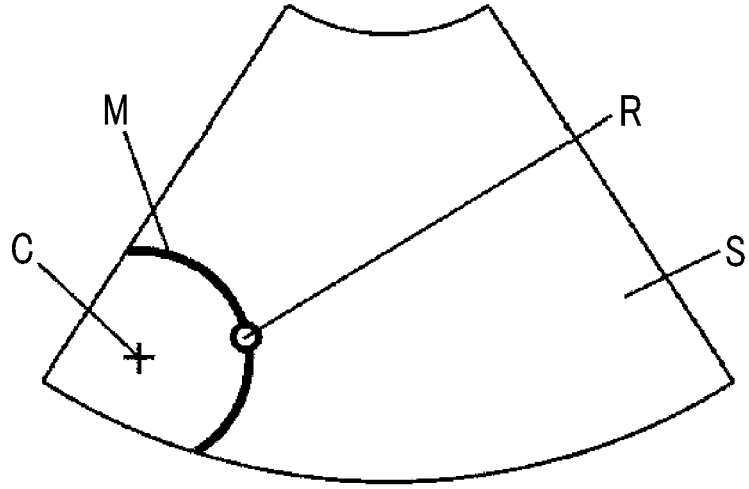
FIG. 14 is a display example of a recommended point in Embodiment 4 of the invention.

In the present disclosure, while the user can operate the caliper C by touching any spot on the caliper operation effective region M, in this case, a recommended candidate of the touch position on the caliper operation effective region M can be shown on the display screen of the touch panel 8. For example, as shown in FIG. 14, in a case where the caliper C is positioned near an end portion of the ultrasound image S, and only a part of the caliper operation effective region M is displayed, a recommended point R representing a recommended candidate of the touch position can be displayed in such a manner as to be superimposed on the displayed caliper operation effective region M. For example, even though the entire caliper operation effective region M is displayed, the recommended point R representing the recommended candidate of the touch position can be displayed in such a manner as to be superimposed at any spot on the caliper operation effective region M.

Here, though not shown, an ultrasound diagnosis apparatus of the Embodiment 4 has the same configuration as the ultrasound diagnosis apparatus 1 of Embodiment 1 shown in FIG. 1, and the display of the recommended point R on the display screen of the touch panel 8 is made by the caliper operation controller 10. In Embodiment 4, the user can touch any spot other than the recommended point R to operate the caliper C as long as the spot is positioned on the caliper operation effective region M.

As described above, as the recommended point R on the caliper operation effective region M is displayed on the display screen of the touch panel 8, it is possible to allow even a user not familiar with the operation of the caliper C using the caliper operation effective region M to simply perform the operation of the caliper C.

Figure 15:
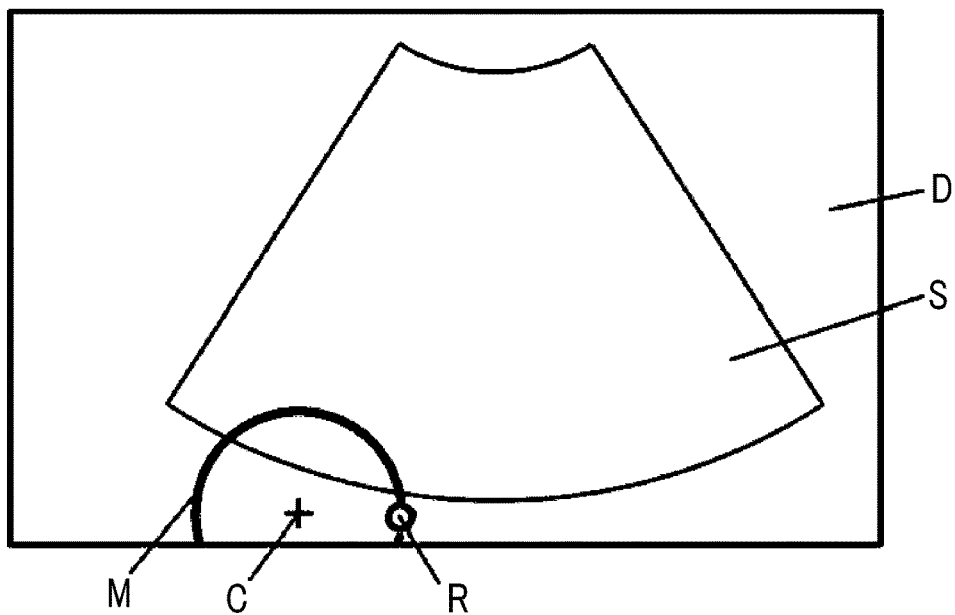
FIG. 15 is another display example of the recommended point in Embodiment 4 of the invention.

In the example shown in FIG. 14, although the caliper C is displayed on the ultrasound image S, the caliper C may be displayed outside the ultrasound image S. For example, as shown in FIG. 15, the caliper C can be displayed outside the ultrasound image S as long as the position is within a display region D of the display screen. In this case, the display of the caliper operation effective region M is not limited as being displayed on the ultrasound image S, and the caliper operation effective region M may be displayed at a position outside the ultrasound image S as long as the position is within the display region D. In the example shown in FIG. 15, since the caliper C is displayed near an end portion of the display region D, the caliper operation effective region M has an arc shape with a part deleted. In this way, even though the caliper C is displayed outside the ultrasound image S, and at least a part of the caliper operation effective region M is displayed outside the ultrasound image S, the recommended point R can be displayed at any spot on the caliper operation effective region M.

Here, the display region D may be a region over the entire display screen of the touch panel 8 or may be a given region determined within the display screen. In a case where the ultrasound image S is stored in the external memory (not shown) or the like, the entire display region D can be set to be stored.

Embodiment 5

Figure 16:
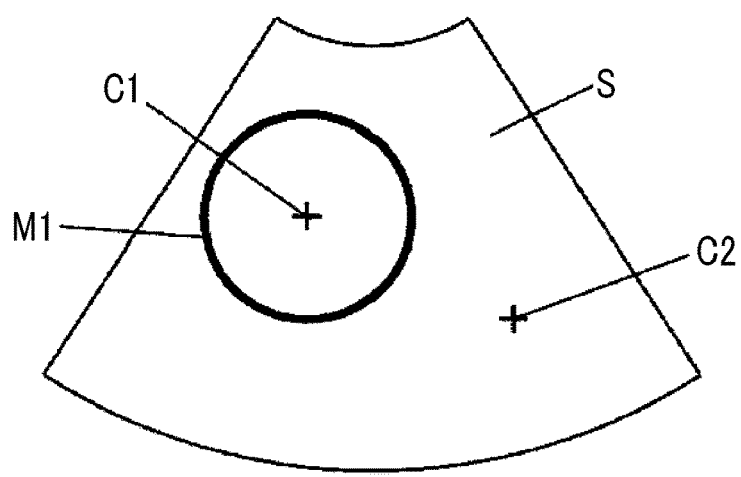
FIG. 16 is a display example of the caliper operation effective region in Embodiment 5 of the invention.

In Embodiments 1 to 4, although an example where one caliper C is displayed on the display screen of the touch panel 8 has been described, a plurality of calipers may be displayed simultaneously. For example, in a case of measuring the distance between two points on the ultrasound image, two calipers can be displayed in such a manner as to be superimposed on the ultrasound image. In this case, for example, as shown in FIG. 16, only one caliper C1 between the two displayed calipers can be set as an operable caliper, and a caliper operation effective region M1 corresponding to only the caliper C1 can be displayed on the display screen of the touch panel 8. In a case where the operation of the caliper C1 is ended, and the operation of the caliper C2 is to be performed, the display of the caliper operation effective region M1 corresponding to the caliper C1 is erased and a state in which the caliper C1 is not operable is brought. Then, a caliper operation effective region (not shown) corresponding to a caliper C2 is displayed and the caliper C2 becomes operable.

Figure 17:
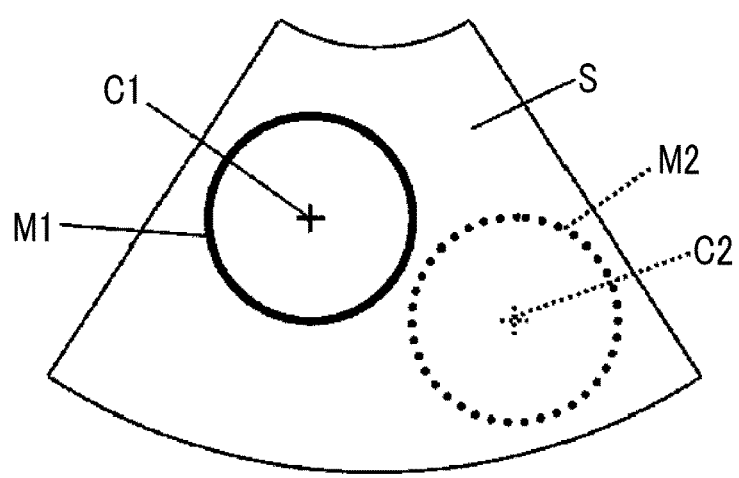
FIG. 17 is another display example of the caliper operation effective region in Embodiment 5 of the invention.

For example, as shown in FIG. 17, both of the two displayed calipers C1 and C2 may be displayed as an operable state. In this case, the caliper operation effective region M1 corresponding to one caliper C1 and a caliper operation effective region M2 corresponding to the other caliper C2 can be displayed.

As described above, even though a plurality of calipers are displayed on the display screen of the touch panel 8, the invention can be applied.

In a case where a plurality of caliper operation effective regions in an operable state are displayed on the display screen of the touch panel 8, the caliper operation controller 10 can display a plurality of caliper operation effective regions such that the caliper operation effective regions are different in color, transparency, kind of line, line thickness, or the like. In this case, each caliper operation effective region and the corresponding caliper may be displayed with the same color, transparency, kind of line, line thickness, or the like. With this, even though the caliper operation effective regions corresponding to a plurality of calipers are displayed on the display screen of the touch panel 8, the respective calipers and the caliper operation effective regions can be easily viewed by the user.

In a case where a plurality of caliper operation effective regions in an operable state are displayed on the display screen of the touch panel 8, only the transparency of the calipers being not operated by the user and the corresponding caliper operation effective regions can be increased. With this, only the caliper being operated by the user can be highlighted and displayed on the display screen of the touch panel 8.

In a case where a plurality of calipers are displayed on the display screen of the touch panel 8, when the touch operation of the user to the caliper operation effective region is released, for each caliper, it is possible to set whether the display of the caliper operation effective region is resumed instantly or is resumed when a given time has elapsed. For example, in a case where two calipers are displayed on the display screen of the touch panel 8 in order to measure the distance between two points, for the caliper operation effective region corresponding to the caliper to be a start point, the display of the caliper operation effective region can be set to be resumed instantly in a case where the touch operation of the user is released. For the caliper operation effective region corresponding to the caliper to be an end point, the display of the caliper operation effective region can be set to be resumed in a case where a given time has elapsed after the touch operation of the user is released.

For example, in a case where the touch operation of the user to the caliper operation effective region is released, according to the purpose of the caliper, it is possible to set whether the display of the caliper operation effective region is resumed instantly to the display of the touch confirmation display region or is resumed to the display of the touch confirmation display region in a case where a given time has elapsed. For example, in a case where the two calipers of the start point and the end point are displayed on the display screen of the touch panel 8 in order to measure the distance between the two points, the user often makes fine adjustment of a measurement value while alternately finely operating the caliper of the start point and the caliper of the end point. For this reason, the display of the caliper operation effective region corresponding to each caliper can be set to be resumed instantly with the release of the touch operation of the user such that the user can smoothly perform the operation of the caliper.

For example, in order to measure an area and a circumference of a tissue included in the ultrasound image, there is a case where a measurement line consisting of a closed curve having a circular shape, an elliptical shape, or the like is displayed on the display screen of the touch panel 8, a plurality of calipers are displayed on the circumference of the measurement line, and the positions of a plurality of calipers are moved to change the size and shape of the measurement line. In this case, the user often operates the caliper while comparing the shape of the tissue in the ultrasound image, the position of each caliper, and measurement values, such as an area inside the measurement line and the circumference of the measurement line. For this reason, the display of the caliper operation effective region corresponding to each caliper can be set to be resumed in a case where a given time has elapsed from the release of the touch operation of the user such that the user easily views the positional relationship between the tissue in the ultrasound image and the caliper, or the like. The display method of the caliper operation effective region of each caliper described above may be set in advance or may be set by the user through the touch panel 8.

From the above description, it is possible to ascertain an ultrasound diagnosis apparatus described in the following supplementary item 1.

[Supplementary Item 1]

An ultrasound diagnosis apparatus comprising:

a touch panel that has a display screen displaying an acquired ultrasound image and allows an input operation of a user;

a caliper generation processor that generates a caliper and displays the caliper on the display screen in such a manner as to be superimposed on the ultrasound image;

a caliper operation control processor that displays, on the display screen, a caliper operation effective region, which surrounds the caliper corresponding to the caliper displayed on the display screen and in which the caliper is moved and operated within the display screen; and an apparatus control processor that, in a case where the user touches the caliper operation effective region displayed on the display screen on the touch panel, performs control such that the caliper operation control processor stops the display of the caliper operation effective region, in a case where the user moves a touch position on the touch panel while touching the caliper operation effective region, performs control such that the caliper generation processor moves a position of the caliper displayed on the display screen following the movement of the touch position, and in a case where the user releases a touch operation on the touch panel, performs control such that the caliper operation control processor resumes the display of the caliper operation effective region, which surrounds the caliper corresponding to the moved position of the caliper.

EXPLANATION OF REFERENCES

1: ultrasound diagnosis apparatus, 2: transducer array, 3: transmission unit, 4: reception unit, 5: AD conversion unit, 6: image generation unit, 7: display controller, 8: touch panel, 9: caliper generation unit, 10: caliper operation controller, 11: apparatus controller, 12: storage unit, 13: signal processing unit, 14: DSC, 15: image processing unit, 21: ultrasound probe, 22: processor, A1, A2: direction, C, C1, C2: caliper, F: finger, L: radius, M, M1, M2: caliper operation effective region, N: touch confirmation display region, P: touch position, R: recommended point, S: ultrasound image.

What is claimed is:

1. An ultrasound diagnosis apparatus comprising:
a touch panel that has a display screen displaying an acquired ultrasound image and allows an input operation of a user; and
a processor configured to:
generate a caliper and display the caliper on the display screen in such a manner as to be superimposed on the ultrasound image; and
display, on the display screen, a caliper operation effective region surrounding the caliper,
wherein the processor is further configured to:
stop displaying the caliper operation effective region in a case where the user touches the caliper operation effective region displayed on the display screen of the touch panel;
move the caliper following a movement operation by the user while in touch with the touch panel and while stopping displaying the caliper operation effective region; and
resume the display of the moved caliper operation effective region that surrounds the moved caliper upon a release of the touch by the user.

2. The ultrasound diagnosis apparatus according to claim 1,
wherein the caliper operation effective region is a region formed in a circle that is centered on the caliper and has a prescribed radius.

3. The ultrasound diagnosis apparatus according to claim 2,
wherein the processor configured to display the caliper operation effective region of a set size on the display screen.

4. The ultrasound diagnosis apparatus according to claim 3,
wherein, in a case where the user touches the caliper operation effective region, the processor configured to display, on the display screen, a touch confirmation display region, which is centered on the touch position and is smaller than the caliper operation effective region, instead of the caliper operation effective region.

5. The ultrasound diagnosis apparatus according to claim 4,
wherein the processor configured to display the touch confirmation display region of a set size on the display screen.

6. The ultrasound diagnosis apparatus according to claim 2,
wherein, in a case where the user touches the caliper operation effective region, the processor configured to display, on the display screen, a touch confirmation display region, which is centered on the touch position and is smaller than the caliper operation effective region, instead of the caliper operation effective region.

7. The ultrasound diagnosis apparatus according to claim 6,
wherein the processor configured to display the touch confirmation display region of a set size on the display screen.

8. The ultrasound diagnosis apparatus according to claim 6,
wherein, in a case where the user touches the caliper operation effective region, the processor configured to gradually reduce the caliper operation effective region displayed on the display screen to perform switching to the display of the touch confirmation display region.

9. The ultrasound diagnosis apparatus according to claim 1,
wherein the processor configured to display the caliper operation effective region of a set size on the display screen.

10. The ultrasound diagnosis apparatus according to claim 9,
wherein, in a case where the user touches the caliper operation effective region, the processor configured to display, on the display screen, a touch confirmation display region, which is centered on the touch position and is smaller than the caliper operation effective region, instead of the caliper operation effective region.

11. The ultrasound diagnosis apparatus according to claim 10,
wherein the processor configured to display the touch confirmation display region of a set size on the display screen.

12. The ultrasound diagnosis apparatus according to claim 10,
wherein, in a case where the user touches the caliper operation effective region, the processor configured to gradually reduce the caliper operation effective region displayed on the display screen to perform switching to the display of the touch confirmation display region.

13. The ultrasound diagnosis apparatus according to claim 1,
wherein, in a case where the user touches the caliper operation effective region, the processor configured to display, on the display screen, a touch confirmation display region, which is centered on the touch position and is smaller than the caliper operation effective region, instead of the caliper operation effective region.

14. The ultrasound diagnosis apparatus according to claim 13,
wherein the processor configured to display the touch confirmation display region of a set size on the display screen.

15. The ultrasound diagnosis apparatus according to claim 14,
wherein, in a case where the user touches the caliper operation effective region, the processor configured to gradually reduce the caliper operation effective region displayed on the display screen to perform switching to the display of the touch confirmation display region.

16. The ultrasound diagnosis apparatus according to claim 13,
wherein, in a case where the user touches the caliper operation effective region, the processor configured to gradually reduce the caliper operation effective region displayed on the display screen to perform switching to the display of the touch confirmation display region.

17. The ultrasound diagnosis apparatus according to claim 13,
wherein the processor configured to gradually magnify the touch confirmation display region displayed on the display screen to perform switching to the display of the caliper operation effective region upon the release of the touch by the user.

18. The ultrasound diagnosis apparatus according to claim 1,
wherein, in a case where the user touches the caliper operation effective region, the processor configured to change a display color of the caliper displayed on the display screen or make the caliper blink.

19. The ultrasound diagnosis apparatus according to claim 1,
wherein the processor configured to display a recommended point representing a recommended candidate of the touch position within the caliper operation effective region on the display screen in such a manner as to be superimposed on the caliper operation effective region.

20. A method of controlling an ultrasound diagnosis apparatus comprising a touch panel that has a display screen and allows an input operation of a user, the method comprising:
displaying an acquired ultrasound image;
generating a caliper and displaying the caliper on the display screen in such a manner as to be superimposed on the ultrasound image;
displaying, on the display screen, a caliper operation effective region surrounding the caliper;
stopping the display of the caliper operation effective region in a case where the user touches the caliper operation effective region displayed on the display screen of the touch panel;
moving the caliper following a movement operation by the user while in touch with the touch panel and while stopping displaying the caliper operation effective region; and
resuming the display of the moved caliper operation effective region that surrounds the moved caliper upon a release of the touch by the user.

* * * * *